US008839680B2

(12) United States Patent
Anderson et al.

(10) Patent No.: US 8,839,680 B2
(45) Date of Patent: *Sep. 23, 2014

(54) METHODS AND APPARATUS FOR ESTIMATING A CONDITION OF A SEAL OF A ROTARY VALVE

(71) Applicants: Shawn William Anderson, Haverhill, IA (US); Ted Dennis Grabau, Marshalltown, IA (US)

(72) Inventors: Shawn William Anderson, Haverhill, IA (US); Ted Dennis Grabau, Marshalltown, IA (US)

(73) Assignee: Fisher Controls International LLC, Marshalltown, IA (US)

( * ) Notice: Subject to any disclaimer, the term of this patent is extended or adjusted under 35 U.S.C. 154(b) by 101 days.

This patent is subject to a terminal disclaimer.

(21) Appl. No.: 13/622,814

(22) Filed: Sep. 19, 2012

(65) Prior Publication Data

US 2014/0076061 A1 Mar. 20, 2014

(51) Int. Cl.
*G01N 3/24* (2006.01)

(52) U.S. Cl.
USPC ............................ 73/843; 73/40; 73/52

(58) Field of Classification Search
CPC ....... G01N 33/30; F01L 3/08; F16K 37/0083; G01M 13/005
USPC ................. 73/40, 52, 841, 843, 845
See application file for complete search history.

(56) References Cited

U.S. PATENT DOCUMENTS

| 4,497,493 | A | * | 2/1985 | Sall et al. ...................... 277/306 |
| 4,501,429 | A | * | 2/1985 | White ........................... 277/368 |
| 4,798,085 | A | * | 1/1989 | Malakhoff et al. ............. 73/148 |
| 5,375,453 | A | * | 12/1994 | Rudd et al. ..................... 73/37 |
| 5,753,799 | A | * | 5/1998 | Shah ............................... 73/40 |
| 5,823,540 | A | | 10/1998 | Grabau et al. |
| 6,345,234 | B1 | | 2/2002 | Dilger et al. |
| 6,840,520 | B2 | | 1/2005 | Faas et al. |
| 7,288,323 | B2 | | 10/2007 | Grabau |
| 7,469,777 | B2 | * | 12/2008 | Burkholder et al. ....... 192/30 W |
| 7,551,268 | B2 | * | 6/2009 | Discenzo ....................... 356/32 |
| 7,766,045 | B2 | | 8/2010 | Fagerlund et al. |
| 7,963,502 | B2 | | 6/2011 | Lovell et al. |
| 7,976,955 | B2 | | 7/2011 | Grabau |
| 8,152,132 | B2 | | 4/2012 | McCarty et al. |
| 2005/0082766 | A1 | | 4/2005 | Lovell et al. |
| 2007/0138429 | A1 | | 6/2007 | Hutchens et al. |
| 2011/0209777 | A1 | | 9/2011 | Lovell et al. |
| 2013/0211735 | A1 | * | 8/2013 | Anderson ...................... 702/34 |

FOREIGN PATENT DOCUMENTS

| EP | 2153986 | 2/2010 |
| EP | 2402635 | 1/2012 |
| WO | 9813422 | 4/1998 |
| WO | 9924808 | 5/1999 |
| WO | 2005051653 | 6/2005 |

(Continued)

*Primary Examiner* — Max Noori

(74) *Attorney, Agent, or Firm* — Hanley, Flight & Zimmerman, LLC

(57) ABSTRACT

Methods and apparatus for estimating a condition of a seal of a rotary valve are disclosed. An example method includes determining a seal wearing cycle of a flow control member of a rotary valve. The seal wearing cycle includes movement of the flow control member between a first position in contact with a seal and a second position. The example method further includes determining a torque of an actuator operating the flow control member for the seal wearing cycle and estimating a condition of the seal based on the torque.

20 Claims, 4 Drawing Sheets

(56) References Cited

FOREIGN PATENT DOCUMENTS

| WO | 2007078426 | 7/2007 |
| WO | 2008016430 | 2/2008 |
| WO | 2008024898 | 2/2008 |
| WO | 2010087938 | 8/2010 |

* cited by examiner

METHODS AND APPARATUS FOR ESTIMATING A CONDITION OF A SEAL OF A ROTARY VALVE

FIELD OF THE DISCLOSURE

This disclosure relates generally to seals and, more particularly, to methods and apparatus for estimating a condition of a seal of a rotary valves.

BACKGROUND

Process control systems generally use a variety of process control devices such as rotary valves to control an industrial process. The rotary valves typically include a flow control member (e.g., a ball, a disk, an eccentric plug, etc.) that engages a seal to close a fluid flow passageway. When the flow control member is moved to engage or disengage the seal, the flow control member may subject the seal to stress and/or causes wear to the seal. To determine a condition of the seal, the valve may be periodically inspected and/or tested offline (i.e., when the industrial process is paused or stopped). Nevertheless, seals often fail while the industrial process is being controlled, or the seals are replaced substantially before the useful lives of the seals are consumed.

SUMMARY

An example method includes determining a seal wearing cycle of a flow control member of a rotary valve. The seal wearing cycle includes movement of the flow control member between a first position in contact with a seal and a second position. The example method further includes determining a torque of an actuator operating the flow control member for the seal wearing cycle and estimating a condition of the seal based on the torque.

Another example method disclosed herein includes determining a seal wearing cycle of a flow control member of a rotary valve. The seal wearing cycle includes movement of the flow control member between a first position in contact with a seal and a second position. The example method further includes, in response to determining the seal wearing cycle, incrementing a count of seal wearing cycles and associating the count with a variable corresponding to an estimated number of seal wearing cycles over a useful life of the seal. Based on the count and the variable, a condition of the seal is estimated.

DETAILED DESCRIPTION

Figure 1:
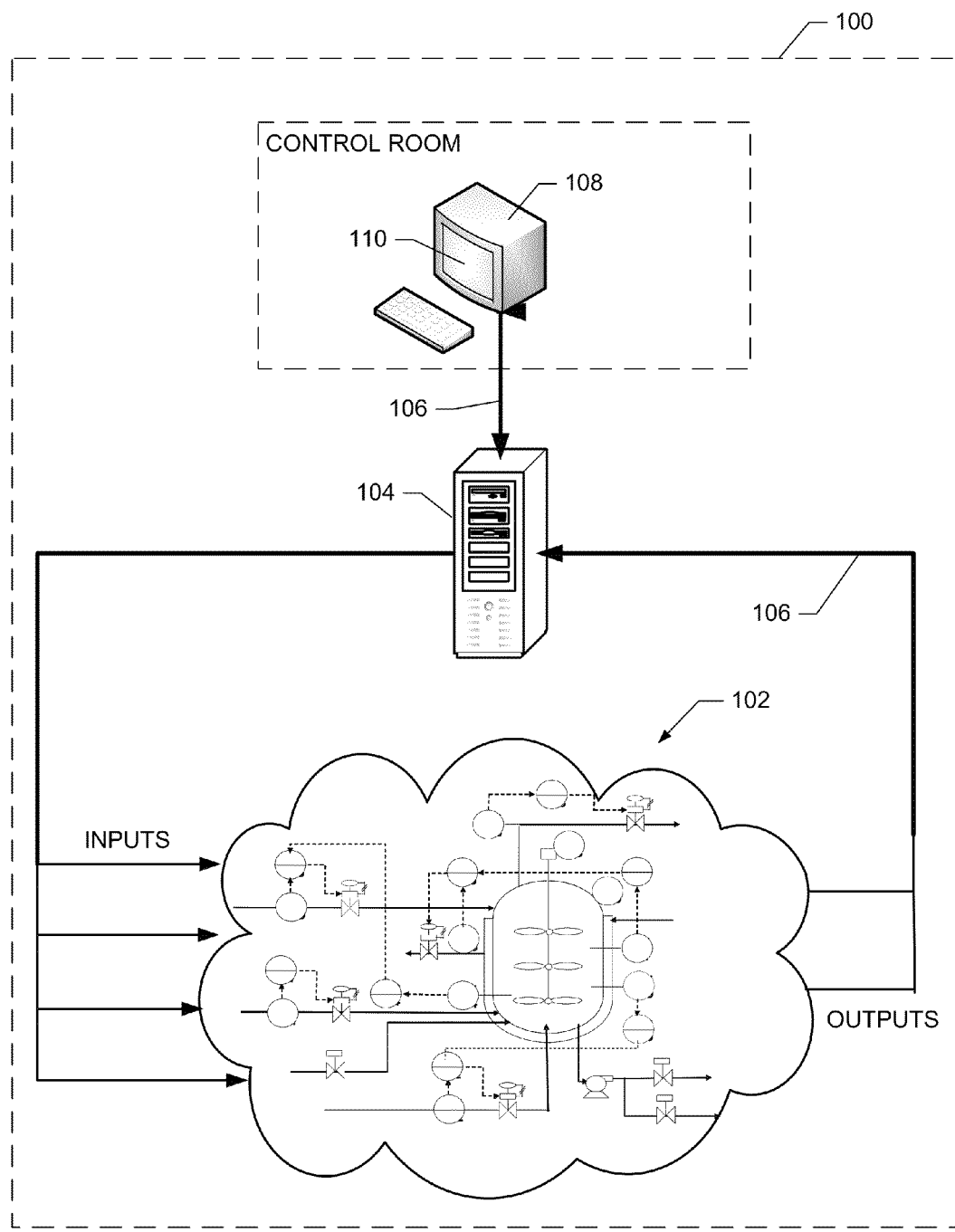
FIG. 1 illustrates an example process control system within which the teachings of this disclosure may be implemented.

While the following apparatus and methods are described in conjunction with ball valves, the example apparatus and methods may also be used with any other rotary valve such as, for example, a full bore ball valve, a segmented ball valve, a V-notch ball valve, a butterfly valve, an eccentric plug valve, etc. Also, although the following apparatus and methods are described in conjunction with pneumatic actuators (e.g., a Fisher® 2052 Diaphragm Rotary Actuator), the example apparatus and methods may also be used with any other rotary actuator such as, for example, a hydraulic actuator, an electric actuator, etc.

Rotary valves such as, for example, full bore ball valves, segmented ball valves, V-notch ball valves (e.g., a Fisher® Vee-Ball™ V150 valve, a Fisher® Vee-Ball™ V300 valve, etc.), butterfly valves, eccentric plug valves and/or other rotary valves are often used in a process control system to control an industrial process. The rotary valves typically include a flow control member (e.g., a disk, a ball, a plug, etc.) that engages and disengages a seal. During a seal wearing cycle when the flow control member is moved from a first, closed position engaging or against the seal to a second position to disengage the seal or from the second position to the first position to engage the seal, the flow control member may subject the seal to stress and/or cause the seal to wear. Over time, the stress and/or the wear may cause the seal to fail.

For a torque seated rotary valve (e.g., a butterfly valve, an eccentric plug, etc.), the actuator outputs full rated torque when the flow control member (e.g., a disk) is engaged with the seal during shutoff. During engagement or disengagement of the flow control member and the seal, the flow control member moves relative to the seal. Thus, a useful life of the seal of the torque seated valve corresponds to a number of seal wearing cycles. Until the seal reaches a threshold condition (e.g., a worn condition), the torque produced by the actuator to achieve shutoff remains substantially constant. If the seal is non-metallic, when the seal reaches the threshold condition, the torque produced by the actuator to achieve shutoff may decrease for subsequent seal wearing cycles as interference between the seal and the flow control member lessens. If the seal is metal and is coated with an anti-galling coating, the torque produced by the actuator to achieve shutoff may increase for subsequent seal wearing cycles due to galling. If the seal is metal and not coated with an anti-galling coating, the torque produced by the actuator to achieve shutoff may decrease for subsequent seal wearing cycles. In other examples (e.g., an eccentric plug valve), the useful life of the seal is not affected by the number of seal wearing cycles. For a position seated valve (e.g., a ball valve), the flow control member is in substantially constant contact with the seal. Thus, the seal wearing cycle includes rotation of the flow control member relative to the seal.

The example apparatus and methods disclosed herein may be used to estimate a condition of a seal of a rotary valve. The example methods and apparatus disclosed herein may be used while the rotary valve is online (i.e., being used to control an industrial process). An example method disclosed herein includes determining a seal wearing cycle of a flow control member of the rotary valve. In some examples, the seal wearing cycle includes movement of the flow control member from a first, closed position against a seal to a second position. In other examples, the seal wearing cycle includes movement of the flow control member from the second position to the first position. Some examples disclosed herein further include determining a torque of an actuator operating the flow control member for the seal wearing cycle and estimating a condition of the seal based on the torque.

Another example method disclosed herein includes determining a seal wearing cycle of the flow control member of the rotary valve and incrementing a count of seal wearing cycles. The count may be associated with a variable corresponding to an estimated number of seal wearing cycles over a useful life of the seal. Based on the count and the variable, a condition of the seal may be estimated. In some examples, the condition of the seal is estimated by calculating a ratio based on the count and the estimated number of seal wearing cycles over the useful life of the seal corresponding to the variable.

FIG. 1 illustrates an example process control system 100 that may be used to implement the example apparatus and methods disclosed herein. The example process control system 100 includes any number of process control devices 102 such as input devices and/or output devices. In some examples, the input devices include valves, pumps, fans, heaters, coolers, mixers, and/or other devices, and the output devices include temperature sensors, pressure gauges, concentration gauges, fluid level meters, flow meters, vapor sensors, valve controllers, and/or other devices.

The input and output devices are communicatively coupled to a controller 104 (e.g., a DeltaV™ controller) via a data bus (e.g., FOUNDATION Fieldbus™) or local area network (LAN) 106. The input and output devices may be wirelessly communicatively coupled to the controller 104. The controller 104 transmits instructions to the input devices to control the process and receives and/or collects information (e.g., measured variables, environmental information, and/or input device information, etc.) transmitted by the output devices. The controller 104 generates notifications, alert messages, and/or other information. The controller 104 is also communicatively coupled to a workstation 108, which includes an interface 110 that displays process control information (e.g., measured process control information, alert message, etc.). Although a single controller 104 is shown in FIG. 1, one or more additional controllers may be included in the example system 100 without departing from the teachings of this disclosure.

Figure 2:
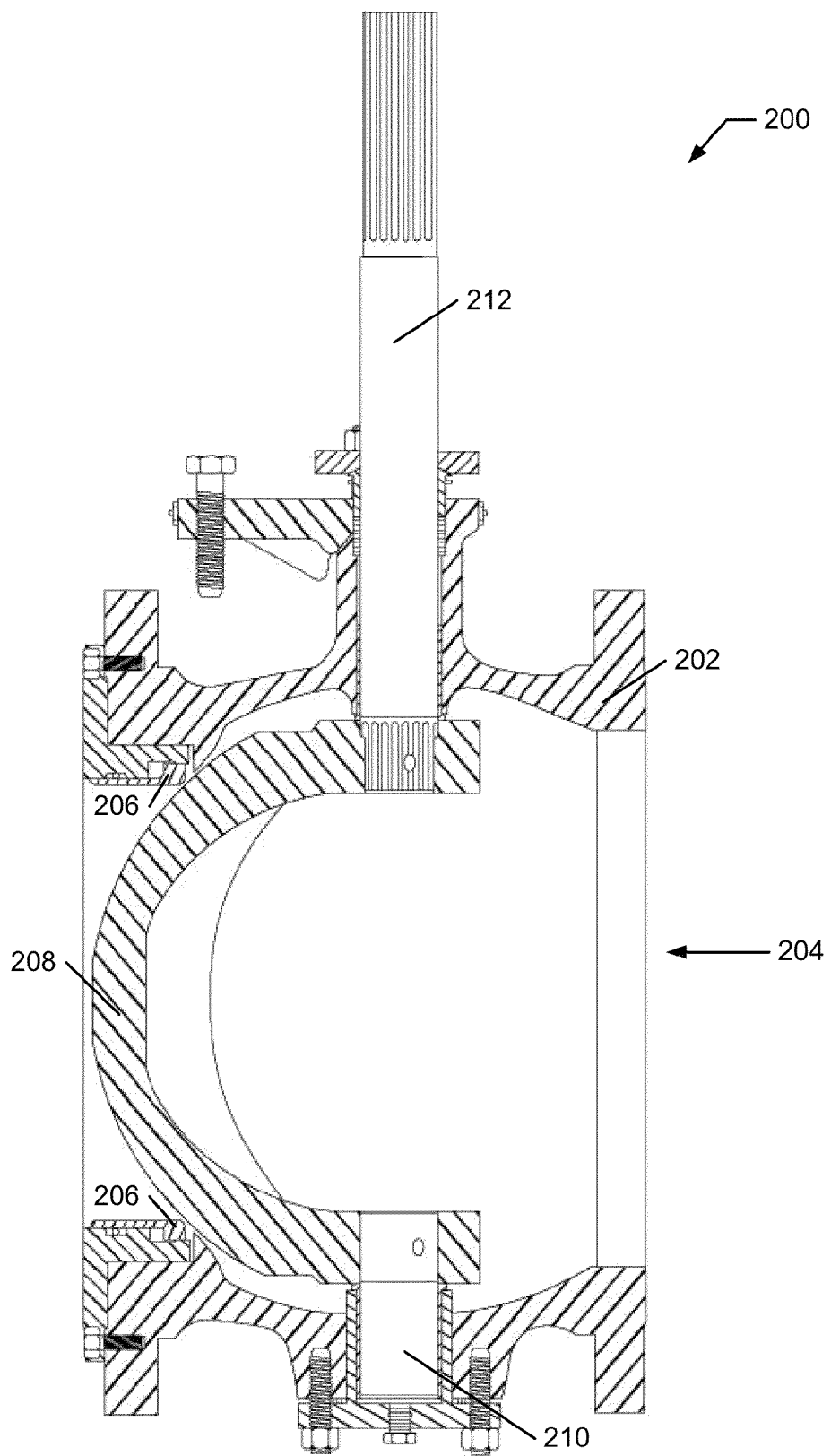
FIG. 2 is a cross-sectional view of an example rotary valve that may be used to implement example methods disclosed herein.

FIG. 2 depicts a cross-sectional view of an example rotary valve 200 that may be used to implement the examples disclosed herein. The example rotary valve 200 is a ball valve (e.g., Fisher® Vee-Ball™ V150 valve). However, any other rotary valve (e.g., a full ball valve, a segmented ball valve, a butterfly valve, a plug valve, an eccentric plug valve, etc.) may be used to implement the examples disclosed herein. The example rotary valve 200 includes a valve body 202 defining a fluid flow passageway 204. A seal 206 is disposed in the fluid flow passageway 204 and coupled to the valve body 202. A flow control member 208 is disposed in the fluid flow passageway 204 adjacent the seal 206. In the illustrated example, the flow control member 208 is a ball. Other examples include other flow control members (e.g., a disk, a plug, etc.) The seal 206 provides a fluid seal between the seal 206 and the flow control member 208 when the flow control member 208 is in a first, closed position engaging or against the seal 206. In the illustrated example, the flow control member 208 is in the first, closed position. The flow control member 208 is operatively coupled to a follower shaft 210 and a driveshaft 212. The driveshaft 212 may be coupled to a pneumatic actuator (not shown) such as, for example a Fisher® 2052 Diaphragm Rotary Actuator. The actuator may be a single acting actuator or a double acting actuator. Other example rotary valves may be used to implement the examples disclosed herein such as, for example, a hydraulic actuator or an electric actuator. The actuator has predetermined characteristics such as, for example, effective area, lever arm length, and bench range (i.e., a range of pressures to rotate the driveshaft 212 under no load from a fully open position to a fully closed position such as, for example 3 psi to 15 psi). Based on the characteristics, an estimated maximum torque of the actuator may be determined.

The example rotary valve 200 also includes a digital valve controller ("DVC") (not shown) such as, for example, a Fisher® FIELDVUE™ DVC6200 Digital Valve Controller. The digital valve controller includes one or more sensors to collect and determine information such as, for example, a position of the driveshaft 212, a direction of shaft rotation, a count of valve closures, a count of valve breakouts, pressures on one or more ends of a piston in the actuator, and/or other information.

The DVC is operatively coupled to the actuator and communicatively coupled to the controller 104. During operation, the DVC receives instructions from the controller 104 to move the flow control member 208, for example, away from the seal 206 (i.e., open the valve), toward the seal 206, and/or to engage the seal 206 to form a fluid seal between the seal 206 and the flow control member 208. The DVC then transmits instructions (e.g., via pneumatic signals) to the actuator, which moves the driveshaft 212.

In the illustrated example, during operation, the DVC determines one or more seal wearing cycles of the flow control member 208. In some examples, the seal wearing cycle is a breakout cycle, which includes movement of the flow control member 208 from the first, closed position to a second position. In other examples, the seal wearing cycle is a valve closure cycle, which includes movement of the flow control member 208 from the second position to the first, closed position. In some examples, the second position is a position of the flow control member 208 where the flow control member 208 is disengaged from the seal 206. In some examples, the second position is a position where the flow control member 208 initially engages or disengages the seal 206 such as, for example, a position corresponding to about two percent of total possible travel of the flow control member 208 away from the first, closed position. In some examples, the second position is a position where the fluid seal between the seal 206 and the flow control member 208 is initially broken or made. During the seal wearing cycle, the DVC determines pressures of the actuator. In some examples in which the seal 206 is in substantially constant contact with the flow control member 208, the seal wearing cycle is rotation of the flow control member 208 relative to the seal 206.

One or more torques of the actuator during the seal wearing cycle may be calculated based on the pressures. For example, a torque of a single acting actuator may be calculated using Equation 1 below; a torque of a double acting actuator without a spring may be calculated using Equation 2 below; and a torque of a double acting actuator with a spring may be calculated using Equation 3 below:

$$T_{Cycle} = (P_{max} - P_{Seat\ End\ Bench\ Range} - P_{spring}) \times A_{Actuator} \times L_{Lever\ Arm}; \quad \text{Equation 1}$$

$$T_{Cycle} = \frac{|P_1 - P_2|_{max}}{2} \times A_{Actuator} \times L_{Lever\ Arm}; \quad \text{Equation 2}$$

$$T_{Cycle} = (|P_1|_{max} - P_{Seat\ End\ Bench\ Range} - P_{spring}) \times A_{Actuator} \times L_{Lever\ Arm}. \quad \text{Equation 3}$$

In Equation 1, $P_{max}$ is a maximum pressure determined by the DVC during the seal wearing cycle. In some examples, $P_{max}$ is an average of two or more pressures determined by the DVC during the seal wearing cycle. In Equations 2 and 3, $P_1$ is a maximum actuator pressure determined by the DVC at one end of the piston of the actuator. In Equation 2, $|P_1-P_2|_{max}$ is a maximum differential actuator pressure determined by the DVC at an opposing end of the piston during the seal wearing cycle. In some examples, $P_1$ and $P_2$ are averages of two or more pressures determined by the DVC during the seal wearing cycle. In Equations 1 and 3, $P_{Seat\ End\ Bench\ Range}$ is a predetermined pressure of the actuator of a no-load condition of initial actuator movement at a seat end of travel of the actuator. In some examples, the $P_{Seat\ End\ Bench\ Range}$ is determined based on data acquired during operation. In other examples, $P_{Seat\ End\ Bench\ Range}$ is determined empirically. In some examples, $P_{Seat\ End\ Bench\ Range}$ is an average of a difference between $P_{max}$ and an actuator pressure at about the first position during a valve closure. $P_{spring}$ is an actuator pressure to overcome a spring of the actuator. In Equations 1-3, $A_{Actuator}$ is an effective area of the actuator diaphragm, piston, or other actuator component used to generate force, and $L_{Lever\ Arm}$ is a length of an arm (e.g., a lever arm, etc.) of the actuator. The above-noted equations are merely examples and, thus, the torque of the actuator may be determined using other equations without departing from the scope of this disclosure.

During each of the seal wearing cycles, the flow control member 208 subjects the seal 206 to stress and causes the seal 206 to wear. As a result, a portion of useful life of the seal 206 is consumed during each of the seal wearing cycles. As the seal 206 wears or fatigues due to the stress, the torque to perform each subsequent seal wearing cycle may increase or decrease.

An estimated life cycle or number of seal wearing cycles over the useful life of the seal 206 may be determined experimentally by, for example, testing one or more rotary valves similar or identical to the example rotary valve 200. In some examples, one of the similar or identical rotary valves is tested by moving a flow control member of the similar or identical rotary valve between the first, closed position and the second position until a seal fails. During the test, a count of seal wearing cycles is determined. Thus, the test yields the estimated number of seal wearing cycles over the useful life of the seal 206. In some examples, the estimated number of seal wearing cycles over the useful life of the seal 206 is stored in a database.

In some examples, a torque is determined for each of the seal wearing cycles during the test. In some such examples, the torque remains substantially constant over a portion (e.g., an initial 1,250,000 seal wearing cycles) of the useful life of the seal until a condition of the seal reaches a threshold level. When the condition of the seal reaches the threshold level (e.g., when the seal wears a threshold amount), the torque for subsequent seal wearing cycles may increase or decrease. Thus, the condition of the seal 206 may be estimated based on the torque for a seal wearing cycle. In some examples, the condition of the seal 206 is estimated based on the torque and a set value (e.g., a maximum available torque output of the actuator, a torque during an initial seal wear cycle, an average torque over a predetermined number of seal wearing cycles (e.g., an average torque over an initial 100 seal wearing cycles), etc.).

In some examples, the estimated number of seal wearing cycles over the useful life of the seal 206 corresponds to one or more variables such as, for example, a seal type (e.g., metal, non-metallic, PTFE, etc.), a valve size, a fluid temperature, and/or any other suitable variable. Thus, the test yields the estimated number of seal wearing cycles over the useful life of the seal 206 corresponding to one or more variables. In some examples, these tests can be used to establish variable ranges (e.g., less than 100 degrees Celsius, between 100 degrees Celsius and 150 degrees Celsius, greater than 150 degrees Celsius, etc.), each of which generally corresponds to a different life cycle or estimated number of seal wearing cycles that can be performed by the valve 200 over the useful life of the seal 206. In some examples, these variables and/or variable ranges are contained in the table or database. Thus, in some examples, a count of the seal wearing cycles performed by the valve 200 is indicative of the condition of the seal 206. For example, if the valve 200 has performed 1,000,000 seal wearing cycles and the estimated number of seal wearing cycles over the useful life of the seal 206 is about 1,500,000 at a given variable or variable range, the seal 206 may be 66.7% worn (i.e., relative to an amount of wear to be subjected to the seal 206 over the useful life of the seal 206).

Figure 3:
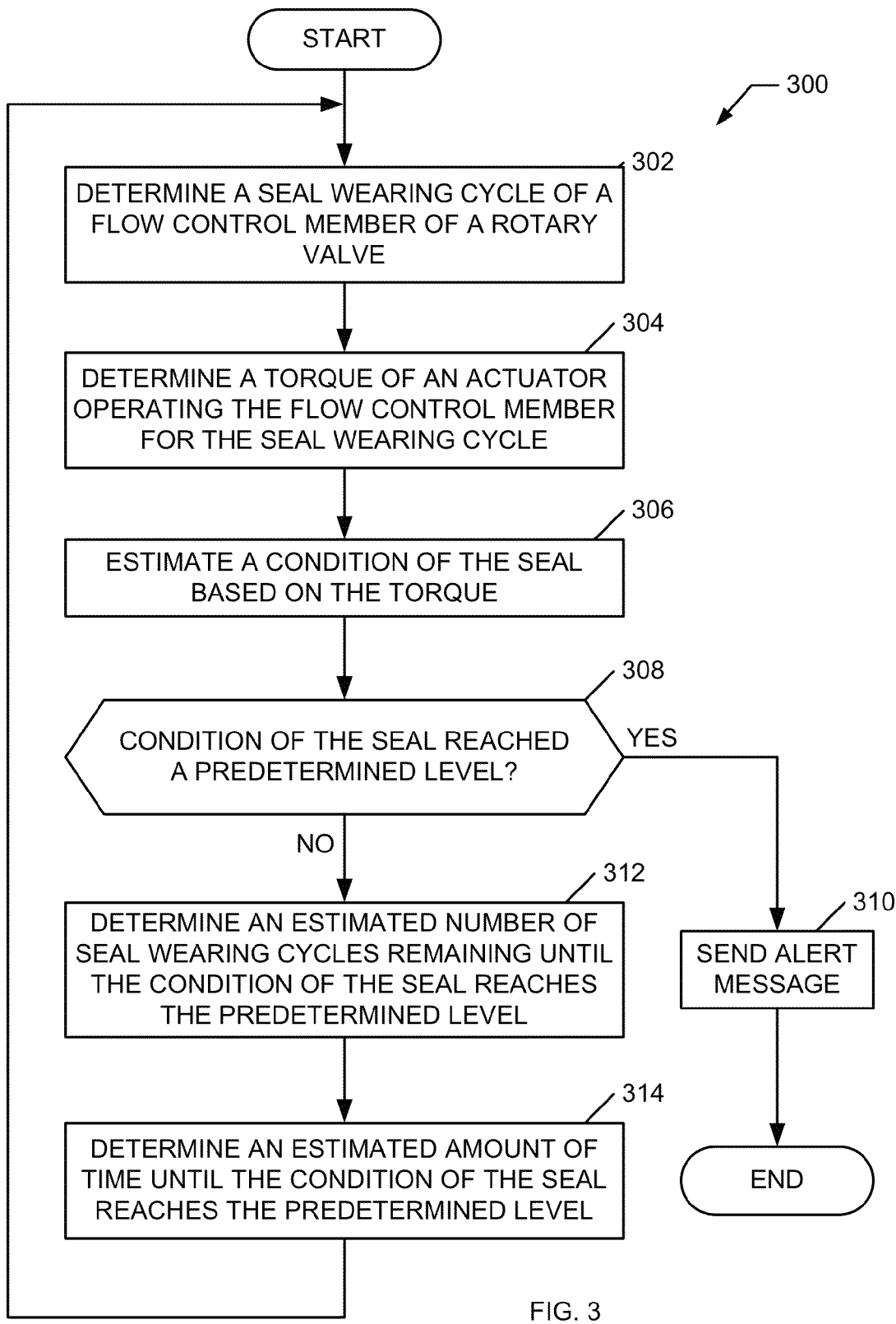
FIG. 3 is a flow chart representative of an example method disclosed herein.
Figure 4:
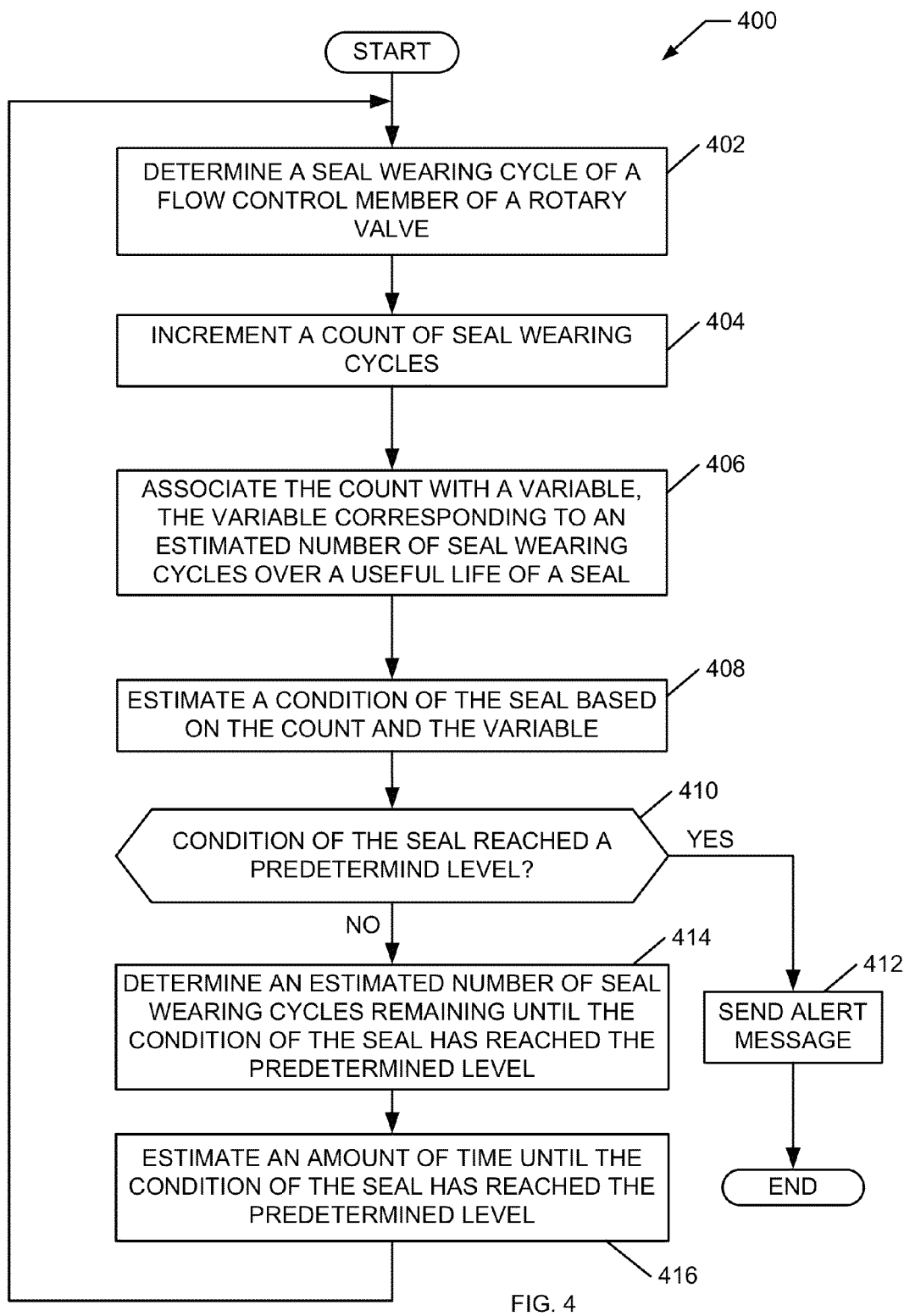
FIG. 4 is a flow chart representative of another example method disclosed herein.

FIGS. 3-4 are flowcharts representative of example methods disclosed herein. Some or all of the example methods of FIGS. 3-4 may be carried out by a processor, the controller 104 and/or any other suitable processing device. In some examples, some or all of the example methods of FIGS. 3-4 are embodied in coded instructions stored on a tangible machine accessible or readable medium such as a flash memory, a ROM and/or random-access memory RAM associated with a processor. Alternatively, some or all of the example methods of FIGS. 3-4 may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, one or more of the operations depicted in FIGS. 3-4 may be implemented manually or as any combination of any of the foregoing techniques, for example, any combination of firmware, software, discrete logic and/or hardware. Further, although the example methods are described in reference to the flowcharts illustrated in FIGS. 3-4, many other methods of implementing the example methods may be employed. For example, the order of execution of the blocks may be changed, and/or some of the blocks described may be changed, eliminated, sub-divided, or combined. Additionally any or all of the example methods of FIGS. 3-4 may be carried out sequentially and/or carried out in parallel by, for example, separate processing threads, processors, devices, discrete logic, circuits, etc.

With reference to FIGS. 1 and 2, the example method or process 300 of FIG. 3 begins by determining a seal wearing cycle of the flow control member 208 of the rotary valve 200 (block 302). In some examples, the seal wearing cycle is a breakout cycle. The breakout cycle includes movement of the flow control member 208 from the first, closed position against the seal 206 to the second position. In other examples, the seal wearing cycle is a valve closure cycle, which includes movement of the flow control member 208 from the second position to the first, closed position. In some examples, the second position is a position of the flow control member 208 where the flow control member 208 is disengaged from the seal 206. In some such examples, the second position is a position of the flow control member 208 where the flow control member 208 initially disengages the seal 206 (e.g., a position corresponding to about two percent of total possible travel of the flow control member 208 away from the first, closed position against the seal 206). In some other examples, the second position is a position where the fluid seal between the seal 206 and the flow control member 208 is initially broken or made.

At block 304, a torque of the actuator operating the flow control member 208 for the seal wearing cycle is determined. During operation, as the flow control member 208 moves, the DVC determines the torque during the seal wearing cycle by determining the positions of the flow control member 208 and/or the driveshaft 212 and determining pressures of the actuator. Using an equation such as, for example, Equation 1, 2 or 3, the torque of the actuator may be calculated using the pressures and the predetermined characteristics of the actuator (e.g., the bench range, the effective area, the lever arm length, etc.).

Based on the torque, a condition of the seal 206 is estimated (block 306). In some examples, estimating the condition of seal 206 includes calculating a value indicative of the condition of the seal 206 based on the torque and a set value. In some examples, the set value is a torque of the actuator during one or more prior seal wearing cycles such as, for example, a torque of the actuator during an initial seal wearing cycle, an average torque over a predetermined number of seal wearing cycles (e.g., the average torque over an initial 100 seal wearing cycles), etc. In other examples, the set value is an estimated maximum available torque of the actuator.

In some such examples, calculating the value indicative of the condition of the seal 206 includes calculating a ratio for the seal wearing cycle such as, for example, the ratio of Equation 4 below:

$$\text{Value Indicative of the Condition of the Seal} = \frac{T}{T_{max}}. \quad \text{Equation 4}$$

In Equation 4, T is the torque for the seal wearing cycle and $T_{max}$ is the estimated maximum available torque of the actuator. In other examples, the ratio for the seal wearing cycles is a ratio of the torque over another set value (e.g., a torque during the initial seal wearing cycle, etc.). In some examples, $T_{max}$ is a predetermined value based on the characteristics of the actuator (e.g., actuator effective area, lever arm length, air supply pressure, etc.). In other examples, $T_{max}$ is a predetermined value based on characteristics of the shaft (e.g., shear strength). In some examples, if $$\frac{T}{T_{max}} = 1,$$

the ratio may indicate that the actuator is unable to move the flow control member 208 into or out of the first position. In some examples, $$\frac{T}{T_{max}}$$

is indicative of a health of a drive train of the actuator.

In some examples, $$\frac{T}{T_{max}}$$

is substantially constant throughout a first portion (e.g., an initial number of seal wearing cycles) of an estimated useful life of the seal 206. For example, during about an initial 1,000,000 seal wearing cycles, $$\frac{T}{T_{max}}$$

may be about 0.8. However, from about 1,000,000 seal wearing cycles to about 1,500,000 seal wearing cycles, $$\frac{T}{T_{max}}$$

may decrease from about 0.8 to 0.75, thereby indicating that the condition of the seal 206 has deteriorated (e.g., the seal 206 has worn).

At block 308, if the condition of the seal 206 has reached a predetermined level is determined. For example, the predetermined level may correspond to the predetermined value using Equation 4 equaling, for example, 0.75. Thus, in the illustrated example, if the torque determined for the seal wearing cycle is seventy-five percent or less of the maximum available torque of the actuator, the condition of the seal 206 has reached the predetermined level. If the condition of the seal 206 has reached the predetermined level, an alert message is sent (block 310). For example, the DVC and/or the controller 104 generates and sends the alert message to the workstation 108.

If the condition of the seal 206 has not reached the predetermined level, an estimated number of seal wearing cycles remaining until the condition of the seal 206 reaches the predetermined level is determined (block 312). In some examples, the estimated number of seal wearing cycles remaining until the condition of the seal 206 reaches the predetermined level is based on the torque for the seal wearing cycle and a rate of change of the torque. For example, during operation, a plurality of seal wearing cycles may occur. In some such examples, the DVC determines a rate of change of the value indicative of the condition of the seal 206 (e.g., $$\left(e.g., \Delta \frac{T}{T_{max}}\right).$$

In some examples, the rate of change of the torque is monotonically related to the number of seal wearing cycles performed by the rotary valve 200. If the predetermined value equals 0.75, the value indicative of the condition of the seal 206 (e.g., $$\left(e.g., \frac{T}{T_{max}}\right)$$

is 0.8 and the rate of change of value (e.g., $$\left(e.g., \Delta \frac{T}{T_{max}}\right)$$

is 0.0001 per 1000 seal wearing cycles, then the estimated remaining number of seal wearing cycles until the condition of the seal 206 reaches the predetermined level is about 500,000.

In some examples, the estimated remaining number of seal wearing cycles until the condition of the seal 206 reaches the predetermined level is based on a count of seal wearing cycles and an estimated number of seal wearing cycles until the condition of the seal 206 reaches the predetermined level (e.g., the estimated useful life of the seal 206). In some such examples, the count is incremented for each seal wearing cycle by the DVC. In some examples, the estimated number of seal wearing cycles until the condition of the seal 206 reaches the predetermined level is determined experimentally by testing one or more rotary valves similar or identical to the rotary valve 200. For example, such a test may yield a result indicating that the estimated number of seal wearing cycles until the condition of the seal 206 reaches the predetermined level (e.g., corresponding to the predetermined value equaling 0.75) is about 1,500,000 seal wearing cycles. If the count is 1,000,000 cycles, and the estimated number of seal wearing cycles until the condition of the seal 206 reaches the predetermined level is 1,500,000 cycles, the estimated remaining number of seal wearing cycles until the condition of the seal 206 reaches the predetermined value is 500,000. Thus, the estimated remaining number of seal wearing cycles until the condition of the seal 206 reaches the predetermined value may be determined based on a result of the test of the similar or identical rotary valve.

At block 314, an estimated amount of time until the condition of the seal 206 reaches the predetermined level is determined. The estimated amount of time may be determined using the rate of change of the value indicative of the condition of the seal 206, a frequency of the seal wearing cycles, and/or the count. In some such examples, the DVC determines the frequency of the seal wearing cycles. The frequency may be an average count of seal wearing cycles per day, hour, week or any other suitable period of time. In the illustrated example, the estimated amount of time until the value indicative of the condition of the seal 206 reaches 0.75 from 0.8 is about five hundred days if the frequency is 1,000 seal wearing cycles per day. The example method then returns to block 302.

FIG. 4 is a flow chart representative of another example method 400 disclosed herein. With reference to FIGS. 1 and 2, the example method or process 400 of FIG. 4 begins by determining a seal wearing cycle of the flow control member 208 of the rotary valve 200 (block 402). In some examples, the seal wearing cycle is a breakout cycle. The breakout cycle includes movement of the flow control member 208 from the first, closed position against the seal 206 to the second position. In other examples, the seal wearing cycle is a valve closure cycle, which includes movement of the flow control member 208 from the second position to the first, closed position. In some examples, the second position is a position of the flow control member 208 where the flow control member 208 is disengaged from the seal 206. In some such examples, the second position is a position of the flow control member 208 where the flow control member 208 initially disengages the seal 206 (e.g., a position corresponding to about two percent of total possible travel of the flow control member 208 away from the first, closed position against the seal 206). In some other examples, the second position is a position where the fluid seal between the seal 206 and the flow control member 208 is initially broken or made.

At block 402, the DVC increments a count of seal wearing cycles. For example, if a count of seal wearing cycles is 999,999 prior to the seal wearing cycle, the DVC increments the count to 1,000,000 for the seal wearing cycle. In some examples, the count of seal wearing cycles is in units of degrees of rotation.

At block 406, the count is associated with a variable corresponding to an estimated number of seal wearing cycles over a useful life of the seal 206. In some examples, the variable is a type of seal, seal material, a valve size, valve construction information, a fluid type to flow through the valve 200, a fluid temperature, an inlet pressure, and/or any other variable. In some examples, the estimated number of seal wearing cycles over the useful life of the seal 206 is determined experimentally by testing one or more rotary valves similar or identical to the rotary valve 200. For example, if the rotary valve 200 has a seal composed of metal, a similar or identical valve including a similar or identical metal seal may be tested to determine the estimated number of seal wearing cycles over the useful life of the seal 206.

In some examples, a value of the variable is determined. For example, a temperature sensor communicatively coupled to the controller 104 may determine the fluid temperature. In some such examples, the count is associated with one of a plurality of variable ranges, each of which corresponds to an estimated number of seal wearing cycles over a useful life of a seal. Such variable ranges can be predetermined experimentally by testing one or more rotary valves similar or identical to the rotary valve 200 at a number of different values of the variable. For example, testing at a fluid temperature of 90 degrees Celsius may yield an estimated number of available seal wearing cycles over the useful life of the seal 206 equal to about 10,000,000; testing at a fluid temperature of 130 degrees Celsius may yield an estimated number of available seal wearing cycles over the useful life of the seal 206 equal to about 7,500,000; and testing at a fluid temperature of 160 degrees Celsius may yield an estimated number of available seal wearing cycles of about 5,000,000. Such testing can be performed to generate any desired number of life cycle estimates, which can then be used to establish ranges such as 100 degrees Celsius or less; between 100 degrees Celsius and 150 degrees Celsius; 150 degrees Celsius or greater, etc. These ranges are just one example of possible ranges and any other number of ranges of any desired span(s) within ranges may be used instead to suit the needs of a particular application. For example, if the temperature sensor determines that the temperature of the fluid for the seal wearing cycle is 110 degrees Celsius, the temperature may be associated with the temperature range of between 100 degrees Celsius and 150 degrees Celsius, which corresponds to the estimated number of available seal wearing cycles over the useful life of the seal 206 equal to about 7,500,000.

Based on the count and the variable, a condition of the seal 206 is estimated (block 408). For example, a value indicative of the condition of the seal 206 may be determined by calculating a ratio based on the count incremented at block 406 and the estimated number of seal wearing cycles over the useful life of the seal 206.

For example, the value indicative of the total amount of useful life of the seal 206 consumed may be calculated using Equation 5 below:

$$\text{Value Indicative of the Condition of the Seal } (\%) = \frac{n_i}{N_i} \times 100. \quad \text{Equation 5}$$

In Equation 5, $n_i$ is the count of seal wearing cycles, and $N_i$ is the estimated number of available seal wearing cycles over the useful life of the seal 206 (e.g., as determined experimentally). For example, if the count of seal wearing cycles is incremented to 1,000,000 at block 406, and the estimated number of seal wearing cycles over the useful life of the seal 206 is equal to about 7,500,000, the value indicative of the condition of the seal 206 is $$\frac{1,000,000}{7,500,000} \times 100$$

or about 13.3 percent, thereby indicating that wear of the seal 206 has reduced the useful life of the seal 206 by about 13.3 percent (i.e., about 87.7 percent of the useful life of the seal 206 remains)

At block 410, if a condition of the seal 206 has reached a predetermined level is determined. For example, the predetermined level may be a consumption of 80 percent of the useful life of the seal 206 as calculated using Equation 5 (e.g., 6,000,000 seal wearing cycles). Other examples use other predetermined levels (e.g., 100 percent consumption of the useful life of the seal 206). If the condition of the seal 206 has reached the predetermined level, an alert message is sent (block 412). For example, the DVC and/or the controller 104 generates and sends the alert message to the workstation 108.

If the condition of the seal 206 has not reached the predetermined level, an estimated number of seal wearing cycles remaining until the condition of the seal 206 has reached the predetermined level is determined (block 414). For example, if the count of seal wearing cycles is 1,000,000 and the estimated number of seal wearing cycles until the condition of the seal 206 reaches the predetermined level is 6,000,000, then about 5,000,000 seal wearing cycles remain until the condition of the seal 206 reaches the predetermined level.

At block 416, an amount of time until the condition of the seal 206 has reached the predetermined level is estimated. In some such examples, the DVC determines a frequency of the seal wearing cycles. In some examples, the frequency is an average count of seal wearing cycles per day, hour, week, or any other suitable period of time. Based on the count, the estimated number of seal wearing cycles until the condition of the seal 206 reaches the predetermined level and the frequency, the amount of time until the condition of the seal 206 has reached the predetermined level may be estimated. For example, if the frequency is 1,000 seal wearing cycles per day and 5,000,000 seal wearing cycles remain until the condition of the seal 206 has reached the predetermined level, about 5,000 days remain until the condition of the seal 206 has reached the predetermined level.

Although certain example methods and apparatus have been described herein, the scope of coverage of this patent is not limited thereto. On the contrary, this patent covers all methods, apparatus and articles of manufacture fairly falling within the scope of the appended claims either literally or under the doctrine of equivalents.

The Abstract at the end of this disclosure is provided to comply with 37 C.F.R. §1.72(b) to allow the reader to quickly ascertain the nature of the technical disclosure. It is submitted with the understanding that it will not be used to interpret or limit the scope or meaning of the claims.

What is claimed is:

1. A method, comprising:
    determining a seal wearing cycle of a flow control member of a rotary valve, the seal wearing cycle including movement of the flow control member between a first position in contact with a seal and a second position;
    determining a torque of an actuator operating the flow control member for the seal wearing cycle; and
    estimating a condition of the seal based on the torque.

2. The method of claim 1, wherein the second position is a position of the flow control member where the flow control member initially engages or disengages the seal.

3. The method of claim 1, wherein estimating the condition of the seal comprises calculating a value based on the torque and a set value.

4. The method of claim 3, wherein calculating the value comprises calculating a ratio using the torque and the set value.

5. The method of claim 1, further comprising sending an alert message when the condition of the seal reaches a predetermined level.

6. The method of claim 1, further comprising
    determining a rate of change of the torque; and
    determining an estimated remaining number of seal wearing cycles until the condition of the seal reaches a predetermined level based on the torque and the rate of change.

7. The method of claim 6, further comprising determining a frequency of the seal wearing cycles and determining an estimated amount of time until the condition of the seal reaches the predetermined level based on the torque and the frequency of the seal wearing cycles.

8. The method of claim 6, further comprising determining a count of seal wearing cycles and determining an estimated remaining number of seal wearing cycles until the condition of the seal reaches the predetermined level based on the count.

9. A method, comprising:
    determining a seal wearing cycle of a flow control member of a rotary valve, the seal wearing cycle including movement of the flow control member between a first position in contact with a seal and a second position;
    in response to determining the seal wearing cycle, incrementing a count of seal wearing cycles;
    associating the count with a variable corresponding to an estimated number of seal wearing cycles over a useful life of the seal; and
    estimating a condition of the seal based on the count and the variable.

10. The method of claim 9, wherein estimating the condition of the seal comprises calculating a ratio based on the count and the estimated count of seal wearing cycles over the useful life of the seal corresponding to the variable.

11. The method of claim 9, wherein estimating the condition of the seal comprises:
    determining a value of the variable for the seal wearing cycle;
    associating the value of the variable with one of a plurality of variable value ranges, each of the variable value ranges corresponding to an estimated number of seal wearing cycles over a useful life of the seal; and
    calculating a ratio based on the count and the estimated number of seal wearing cycles over the useful life of the seal.

12. The method of claim 11, further comprising determining each of the estimated number of seal wearing cycles over the useful life of the seal by testing another rotary valve similar or identical to the rotary valve.

13. The method of claim 9, further comprising determining an estimated number of seal wearing cycles remaining until the condition of the seal reaches a predetermined level.

14. The method of claim 13, further comprising determining a frequency of seal wearing cycles and estimating an amount of time remaining until the condition of the seal reaches the predetermined level based on the count and the frequency.

15. The method of claim 9, wherein the second position is a position where the flow control member initially engages or disengages the seal.

16. A tangible machine readable storage medium having instructions stored thereon that, when executed, cause a machine to:
    determine a seal wearing cycle of a flow control member of a rotary valve, the seal wearing cycle including movement of the flow control member between a first, closed position against a seal and a second position;
    determine a torque of an actuator operating the flow control member for the seal wearing cycle; and
    determine a value indicative of a condition of the seal based on the torque and a set value.

17. The tangible machine readable storage medium as defined in claim 16, wherein the machine readable instructions, when executed, determine the value indicative of the condition of the seal by calculating a ratio of the torque and a maximum available torque of the actuator.

18. The tangible machine readable storage medium as defined in claim 16, wherein the second position is a position of the flow control member where the flow control member initially engages or disengages the seal.

19. The tangible machine readable storage medium as defined in claim 16, wherein the machine readable instructions, when executed, further cause the machine to determine an estimated number of seal wearing cycles remaining until the condition of the seal reaches a predetermined level.

20. The tangible machine readable storage medium as defined in claim 19, wherein the machine readable instructions, when executed, cause the machine to determine the estimated number of seal wearing cycles remaining until the condition of the seal reaches the predetermined level based on a test of a similar or identical rotary valve.

* * * * *

UNITED STATES PATENT AND TRADEMARK OFFICE
CERTIFICATE OF CORRECTION

PATENT NO.          : 8,839,680 B2                                          Page 1 of 1
APPLICATION NO.     : 13/622814
DATED               : September 23, 2014
INVENTOR(S)         : Shawn William Anderson and Ted Dennis Grabau It is certified that error appears in the above-identified patent and that said Letters Patent is hereby corrected as shown below:

In the drawings,

Figure 4, Block 410: Replace "predetermind" with --predetermined--

Signed and Sealed this
Twenty-fourth Day of February, 2015

Michelle K. Lee
*Deputy Director of the United States Patent and Trademark Office*